(12) United States Patent
Jones et al.

(10) Patent No.: US 9,933,360 B2
(45) Date of Patent: Apr. 3, 2018

(54) DEVICE AND METHOD FOR DETERMINING THE COMPOSITION OF A MIXTURE OF FLUIDS

(75) Inventors: Robert Jones, Cambridge (GB); Matthew James Hayes, Cambridge (GB); Paul David Ryder, Cambridge (GB)

(73) Assignee: Pietro Fiorentini S.P.A., Arcugnano (VI) (IT)

( * ) Notice: Subject to any disclaimer, the term of this patent is extended or adjusted under 35 U.S.C. 154(b) by 173 days.

(21) Appl. No.: 13/322,439

(22) PCT Filed: Jun. 4, 2010

(86) PCT No.: PCT/GB2010/001109
§ 371 (c)(1),
(2), (4) Date: Jan. 24, 2012

(87) PCT Pub. No.: WO2010/139965
PCT Pub. Date: Dec. 9, 2010

(65) Prior Publication Data
US 2012/0112072 A1    May 10, 2012

(30) Foreign Application Priority Data
Jun. 4, 2009 (GB) .................................. 0909662.9

(51) Int. Cl.
*G01N 21/359* (2014.01)
*G01N 33/28* (2006.01)
(Continued)

(52) U.S. Cl.
CPC ....... *G01N 21/359* (2013.01); *G01N 21/3577* (2013.01); *G01N 33/2847* (2013.01);
(Continued)

(58) Field of Classification Search
CPC .................................................. G01N 21/3577
(Continued)

(56) References Cited

U.S. PATENT DOCUMENTS 3,797,942 A * 3/1974 Joly .............................. 356/410
4,914,719 A    4/1990 Conlon et al.
(Continued)

FOREIGN PATENT DOCUMENTS

DE    102005025675 A1    11/2006
WO    2005106387 A1    11/2005

*Primary Examiner* — Yara B Green
(74) *Attorney, Agent, or Firm* — Workman Nydegger

(57) ABSTRACT

A device for determining the composition of a mixture of fluids by spectral absorption, comprises: a radiation source; a detector for detecting radiation that has been attenuated by the mixture; and a device for separating the radiation into a wavelength band corresponding to an absorption band of one of the fluids, a wavelength band corresponding to an absorption band of another of the fluids, and at least one reference wavelength band substantially adjacent to each of the absorption bands, and especially adjacent to each side of the absorption band or group of absorption bands. The device may be used to determine the composition of mixtures of oil, water and gaseous hydrocarbons in oil wells where there is a very large degree of time varying scattering e.g. Rayleigh and Mie scattering due to turbulence.

19 Claims, 13 Drawing Sheets

(51) Int. Cl.
*G01N 21/3577* (2014.01)
*G01N 21/31* (2006.01)

(52) U.S. Cl.
CPC .............. *G01N 2021/3137* (2013.01); *G01N 2021/3148* (2013.01); *G01N 2021/3188* (2013.01); *G01N 2201/069* (2013.01)

(58) Field of Classification Search
USPC .... 250/339.12, 339.13, 345, 339.02, 339.07, 250/339.01
See application file for complete search history.

(56) References Cited

U.S. PATENT DOCUMENTS

| | | | | |
|---|---|---|---|---|
| 4,980,554 | A * | 12/1990 | Ahn | 250/394 |
| 5,017,785 | A * | 5/1991 | Rasanen | 250/345 |
| 5,365,067 | A * | 11/1994 | Cole | G01N 21/21 250/339.07 |
| 5,406,082 | A * | 4/1995 | Pearson et al. | 250/339.11 |
| 5,475,221 | A * | 12/1995 | Wang | 250/339.07 |
| 5,908,789 | A * | 6/1999 | Weckstrom | G01N 21/3504 250/339.01 |
| 6,191,421 | B1 * | 2/2001 | Yamamori | G01N 21/15 250/339.01 |
| 6,844,554 | B2 * | 1/2005 | Karlsson | 250/339.13 |
| 2006/0186340 | A1 | 8/2006 | Lievois et al. | |
| 2007/0035737 | A1 | 2/2007 | Andrews et al. | |
| 2007/0114372 | A1 | 5/2007 | Lievois et al. | |

* cited by examiner

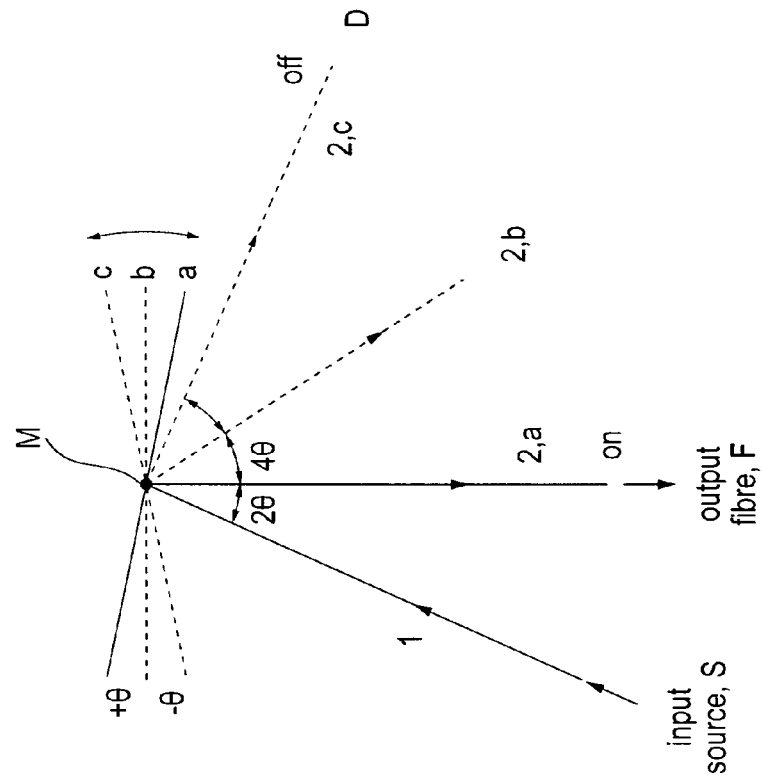
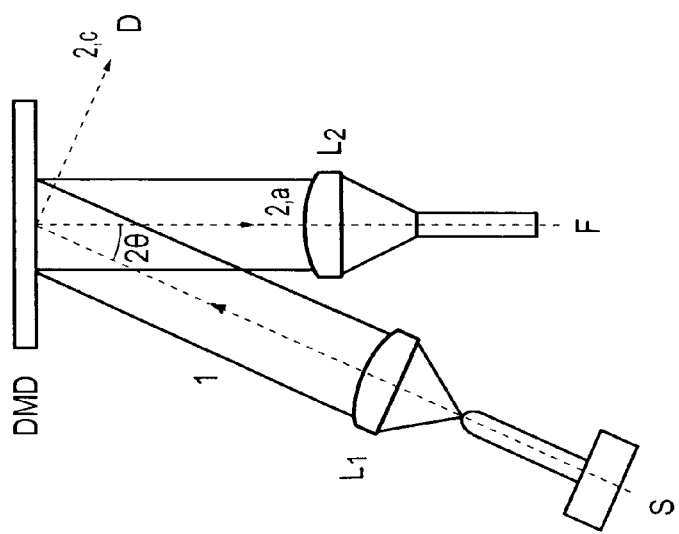
FIG. 7a
FIG. 7b

DEVICE AND METHOD FOR DETERMINING THE COMPOSITION OF A MIXTURE OF FLUIDS

FIELD OF THE INVENTION

This invention relates to the monitoring of fluids, especially to the determination of the composition of mixtures of fluids. The invention is directed in particular to the determination of the composition of a mixture of water and hydrocarbons, but aspects of the invention may be employed with other fluids.

The invention is particularly applicable to the determination of the water content or "water cut" in an oil natural gas well or an oil pipeline. The water may be present naturally in the hydrocarbon stream and may cause corrosion to equipment, so that it may be desirable to ascertain the water fraction of the stream in order to ensure that any corrosion inhibition scheme is adequate. In other circumstances, for example in the case of an oil well, it may be necessary to pump water down the downhole in order to recover the oil, in which case relatively high quantities of water may be present, for example up to 90% of the mixture or more, and it may be necessary to determine the water fraction in order to ascertain the economic viability of the well.

BACKGROUND OF THE INVENTION

The water fraction and oil fraction will typically be determined by near infrared (NIR) absorption, for example by means of a differential optical absorption spectrometer (DOAS) in which the attenuation of radiation at a wavelength of an absorption band characteristic of one component of the mixture is compared with the absorption of a reference wavelength in order to determine the proportion of the relevant component in the mixture. Clearly it is desirable to be able to determine the water cut with a high degree of accuracy. For example, at a high water fraction, a small error in the value of the water fraction will lead to a considerable error in the fraction of oil.

Conventional DOAS techniques employ an operating wavelength $\lambda_m$ at the centre of the absorption band of a specific molecular constituent of interest, and a non-resonantly absorbing reference wavelength $\lambda_r$. It may be shown that the molecular concentration $N_m$ is related to the ratio of the transmitted optical power P at the two wavelengths by the following equation:

$$\frac{P(d, \lambda_m)}{P(d, \lambda_r)} = \exp(-N_m \cdot \sigma_m(\lambda_m) \cdot d)$$

from which on can obtain:

$$\Rightarrow N_m = \frac{1}{\sigma_m(\lambda_m) \cdot d} \ln\left(\frac{P(d, \lambda_r)}{P(d, \lambda_m)}\right) \quad (1)$$

in which $\sigma_m$ is the molecular absorption cross-section, and d is the thickness of the material sample.

One example of a near infrared sensor is disclosed in U.S. Pat. No. 6,292,756 which describes a narrow band infrared water fraction meter in which the infrared radiation is substantially transmitted through the hydrocarbon phase and absorbed by the water phase so that the attenuation of the radiation will give an indication of the water fraction of the mixture.

However, it is still difficult with such a system to obtain an accurate indication of the water fraction of the oil and water mixture. This is largely due to the fact that stream of fluid passing the spectrometer probe will, in general, have a number of spectrally broadband variations in the optical transmission. This is due predominantly to the Mie and Rayleigh scatter from fluid borne particulates such as sand, fine bubbles and emulsions that are likely to be present as random, time dependent quantities with the result that there will be a relatively high background noise to the spectroscopic measurement. Also, the background noise will not be constant but will vary rapidly with time as bubbles, solid matter and the like move past the probe in the flow of the liquid.

BRIEF SUMMARY OF THE INVENTION

According to one aspect, the present invention provides a device for determining the composition of a mixture of fluids by spectral absorption, which comprises:

a radiation source for illuminating the mixture with radiation having a range of wavelengths that extends over an absorption band in each of the fluids;

a detector for detecting radiation that has been attenuated by the mixture; and a device for separating the radiation into a wavelength band corresponding to an absorption band of one of the fluids, a wavelength band corresponding to an absorption band of another of the fluids, and at least one reference wavelength band substantially adjacent to each of the absorption bands.

Thus, according to the invention, DOAS is performed with a broadband source and with post-spectral division of the wavelength. The broadband source is preferably one that will emit radiation over the entire range of absorption bands that are being investigated, for example in the near infrared (NIR) band from 1 µm to 2 µm in the case of hydrocarbon/water mixtures. The invention has the advantage that the reference wavelength will normally be adjacent to the wavelength range of the absorption band, the intensity (i.e. the extinction coefficient) of the reference wavelength will provide a good indication of the baseline of the absorption band. In contrast to this, in the known NIR systems, the correction for broadband attenuation is referenced to the transmission at a single wavelength band (e.g. 900 nm to 1300 nm) remote from the molecular resonant absorption bands of the critical fluid constituent, e.g. water centred at 1450 nm, and methane/oil centred between 1600 nm and 1800 nm. Systems with such remote referencing can only compensate partially for spectrally broadband attenuation which can have a significant variation over the range of spectral measurement. Critical flow parameters such as the water cut ($W_c$) and oil flow rate (OFR) measured under these conditions are therefore inherently subject to relatively large errors.

Preferably the device for separating the radiation is operable to separate the radiation into two reference bands, one reference band located adjacent to each side of the absorption band of one of the fluids. The intensity of the noise in the spectrum may not be constant with respect to the wavelength of the radiation across the observed range. For example, in the case of Rayleigh scattering the degree of scattering is proportional to $\lambda^{-4}$, so that for systems that generate a large degree of scatter, the absorption bands are superposed on a background that slopes with wavelength of the radiation, and so taking a reference for the absorption on one side of the absorption band may lead to a false result. If a pair of reference wavelengths are employed, one on each side of the absorption band or on each side of a group of absorption bands, it is possible to interpolate the extinction coefficient of the reference wavelengths on either side of the absorption band in order to provide a relatively accurate baseline for the absorption band even where the noise level plot "slopes" with respect to wavelength.

Although, according to the broadest aspect of the invention, only a single absorption band need be observed, it is preferable to measure the extinction coefficient of a characteristic absorption band for a number of components of the mixture, especially for each component of the mixture of interest, and to measure the extinction coefficient of reference wavelengths on either side of each absorption band. In the case of oil recovery, this may require observing a water absorption band and a hydrocarbon absorption band. Also, it is often the case that liquid hydrocarbons are recovered in the presence of gaseous hydrocarbons, principally methane, and so it may be necessary to measure the absorption of liquid hydrocarbons and gaseous hydrocarbons separately.

Although it is possible in principle to employ a spectrometer in order determine the absorption of the radiation in the absorption band and in the reference bands, such a device will in general have insufficient sensitivity and bandwidth to measure the small variations in fluid composition required at the operational flow rates of typically 1 msec$^{-1}$ to 30 msec$^{-1}$. In addition the use of discrete detectors and filters offers significant scope for the reduction in cost relative to that of a conventional NIR spectrometer.

In order to observe an adequate number of wavelength bands corresponding to the absorption bands of each component in the mixture and the reference bands adjacent thereto, the device for separating the radiation preferably comprises:

a first radiation divider that is operable to separate radiation into a wavelength band having a wavelength extending over the absorption band of one of the fluids and at least one reference wavelength band substantially adjacent to the absorption band; and a second radiation divider that is operable to receive radiation from the first radiation divider and to separate it into radiation having a wavelength extending over the absorption band and radiation having a wavelength corresponding to the or each reference wavelength band.

This may be achieved for example by means of one or more optical notch filters or band stop filters, one or more optical beam splitters, or combinations of the two. The device preferably includes a dichroic beam splitter and/or a Rugate filter. The latter has multiple reflective and reciprocal transmissive spectral notches as a result of its periodic refractive index variation. For example, the device may include a plurality of dichroic beam splitters to split the radiation into a plurality of wavelength bands, the radiation in each wavelength band being split into an absorption band and a reference band having a wavelength range substantially adjacent to the absorption band by means of a Rugate notch or band stop filter. Thus, in the preferred form of device according to the invention, the characteristics of the spectroscopic measurement are essentially "hard-wired" in the device, thereby enabling a high degree of precision at relatively low cost.

An empirical approach is used in determining the power of the absorbed signals, which considers the ratio of the integrated optical powers in the molecular absorption and reference bands:

$$R_{DOAS} = \frac{\sum_{\lambda_{r1}^{min}}^{\lambda_{r1}^{max}} \Phi(d, \lambda) \cdot \delta\lambda + \sum_{\lambda_{r2}^{min}}^{\lambda_{r2}^{max}} \Phi(d, \lambda) \cdot \delta\lambda}{\sum_{\lambda_{m}^{min}}^{\lambda_{m}^{max}} \Phi(d, \lambda) \cdot \delta\lambda} \quad (2)$$

where $\Phi$ is the optical power spectral density (power per unit wavelength). It should be noted that the integral of $\Phi$ with respect to wavelength gives the optical power in the measurement band, and so $R_{DOAS}$ is equivalent to the power ratio inside the logarithm in Equation (1) above.

In system simulation, it has been shown that by tuning the values of $\lambda_m^{min}$, $\lambda_m^{max}$, $\lambda_{r1}^{min}$, $\lambda_{r1}^{max}$, $\lambda_{r2}^{min}$ and $\lambda_{r2}^{max}$ for each material of interest (crude oil, water and methane), the DOAS ratio, $R_{DOAS}$, defined in Equation (2) can give consistent results for a variety of material samples and operating conditions. In this way, DOAS ratio calibration curves may be derived which allow the fractional volume (and associated error) of each material constituent to be inferred by reference spectrometer data, by integrating the transmitted power spectral density over the relevant molecular absorption and reference bands. Any form of spectroscopic instrument used for this type of application is referred to generally as a Spectroscopic Optical Fluid Analyser (SOFA). The fractional volumes deduced for crude oil, water and methane may then be used to calculate the oil cut Oc and the water cut Wc using the standard equations:—

$$W_C = \frac{W_f}{O_f + W_f} \quad (3)$$

where,
$W_f$=water fraction
$O_f$=oil fraction
The Oil Cut, $O_C$, is given by, $$O_C = \frac{O_f}{O_f + W_f} \quad (4)$$

From equation (3), $$O_C = 1 - W_C \quad (5)$$

And hence the required oil flow rate is given by, $$Q_O = Q_1(1 - W_C) \quad (6)$$

where $Q_1$ is the independently measured total flow rate.

Another important measurement that may be performed using the system is the Gas to Oil Ratio GOR. This may be used advantageously for sub-sea applications at high pressures where the gas is predominantly in solution. The measurement of GOR under these conditions eliminates the need for sub-sea sampling and provides data that will indicate the oil shrinkage at the surface separator due to the gas coming out of solution. The measurement of GOR of bore hole fluids in exploration also helps establish the viability of a well before opening for full use.

In order to develop the optimum sensor, experimental spectra need to be collected using the Spectroscopic Optical Fluid Analyser (SOFA). This data should ideally cover a range of oil and water cuts measured in a variety of operating conditions from a number of oil wells. This will allow the DOAS ratio algorithm to be tuned for each substance to give optimum performance. The optimised set of DOAS ratio algorithms can then be used as the basis for a Rugate filter design for the final production sensor. Alternatively, the DOAS system may, in the absence of the above data, be based on laboratory measurements of pure water and oil but as a result may be less fine tuned for field measurement. This constitutes the 'hard wiring' of spectroscopic data referred to above.

It is also worth noting methods for calibrating the proposed measurement technique for repeatable performance with different optical sources. For lamp-based SOFA systems (for example a broadband source), lamps are preferably chosen with integrated temperature control and which give defined spectral outputs. The precise spectrum for each new lamp can be recorded during system setup and also monitored periodically during SOFA experiments. These reference spectra can be used for normalizing the transmission spectra of the material samples prior to application of the DOAS ratio algorithm.

For an LED based DOAS sensor, temperature control of the LEDs is desirable to maintain repeatable source spectra during sensor operation. The spectrum of each LED may be measured with a spectrometer during the build of a new sensor unit. The DOAS ratio calibration curves for each sensor unit could be adjusted depending on the values of the peak wavelengths of its constituent LEDs. This could be implemented using a look-up table of calibration adjustment factors calculated during detailed system design. In this way, a routine calibration procedure could be performed during sensor manufacturing to store digitally a set of calibration values in each unit for use throughout its operating lifetime.

While the sensor according to the first aspect of the invention may be used to obtain a relatively accurate indication of the intensity of the various absorption bands, there remains a problem of processing the signals obtained. The signals will in general be superimposed on a background absorption/scatter signal, which can have a very large dynamic range due to the varying scatter caused by particles and droplets in the mix, which can have a significantly larger dynamic range than the relatively small ratio of the signals. According to a second aspect of the invention the large dynamic range of the signals may be mitigated by the processing architecture chosen. If this were not the case, then an extremely high resolution ADC would be required to cover the full dynamic range of the signals while still being sensitive enough to measure the small difference between the signals. This would be hard to source, expensive, and hard to design.

Thus, according to a second aspect, the invention provides a device for outputting the ratio of values of a pair of signals where the value of the individual signals may vary by an amount significantly greater than the ratio of values of the signals, which comprises:

a detector for sampling each signal;

a variable-gain amplifier for amplifying each of the detected signals with the same gain and outputting each of the amplified signals;

wherein the variable-gain amplifier includes a feedback loop for receiving one of the amplified signals output by the amplifier and adjusting the gain of the amplifier to be inversely proportional thereto, so that the other of the pair of signals is output by the amplifier with reference to the said one of the signals.

In the broadest aspect, the two signals may be any signals. However, where the signals are detected by means of a detector according to the first aspect of the invention, one of the signals may be a measurand signal, for example a signal defining the intensity of an absorption band of the fluid being monitored, while the other signal may be a reference or background signal for example the background signal observed on either side of the absorption band. Alternatively, it is possible for one of the signals to be a signal defining the intensity of the absorption band while the other signal is a signal defining the intensity of a different absorption band so that the ratio of the intensities of the two absorption bands may be obtained directly.

Since the background signal may vary much faster than the ratio of the two signals the design of the processor preferably therefore has sufficient bandwidth and dynamic range to cope with the variation of the absolute signals sizes, while still having enough sensitivity to correctly measure the ratio. This means that any amplifiers, filters or closed-loop blocks in the architecture are preferably able to respond fast enough to track the change in the background level until the dynamic range has been reduced. However, since the ratio of the two signals (which is the desired measurement) changes much more slowly, it would be easier and cheaper if this information was presented to the digital circuitry at a speed compatible with the rate of change of the ratio rather than the background.

Preferably the feedback loop includes a filter for setting the gain of the variable-gain amplifier with respect to a reference voltage so that the gain of the variable-gain amplifier is equal to the reference voltage divided by the value of the said one of the signals. The amplifier is preferably operable to output both the measurand signal and the background signal, while the feedback loop may be operable to adjust the gain of the amplifier to be inversely proportional to the intensity of the background signal.

It may not be the case that a single amplifier will enable the circuit to have a sufficient gain to accommodate the entire dynamic range of the signal, and so the device may include a plurality of the variable gain amplifiers in cascade, each such variable gain amplifier having a feedback loop.

Also, according to a preferred way of carrying out the design, the device includes a multiplexer for multiplexing the two signals, for example the detected measurand signal and background signal before they are input to the variable-gain amplifier, and a demultiplexer in the feedback loop for demultiplexing the output of the variable gain amplifier, so that only one of the measurand signal and the background signal is fed back to the amplifier to adjust the gain thereof.

According to yet another aspect, the invention provides a method of determining the ratio of values of a pair of signals where the value of the individual signals may vary by an amount significantly greater than the ratio of values of the signals, which comprises:

sampling each signal;

amplifying each of the detected signals by means of a variable gain amplifier with the same gain; and outputting one of the amplified signals;

wherein the variable-gain amplifier includes a feedback loop for receiving one of the amplified signals output by the amplifier and adjusting the gain of the amplifier to be inversely proportional thereto, so that the other of the pair of signals is output by the amplifier with reference to the said one of the signals.

One problem with systems for monitoring the composition of fluids, and especially for monitoring the composition of fluids flowing in oil pipelines is that the radiation sources employed may have only a limited lifetime, and it is therefore necessary to repair or replace them. It is thus desirable to maximise the lifetime of such radiation sources or the period between replacement, which may be achieved by running them at minimum power. This is particularly desirable for sub-sea applications where there is no routine access for maintenance of the system. The output optical power that is required of the radiation source will depend on the measurement bandwidth, which will itself depend on the flow rate of the fluid. Thus, according to yet another aspect, the invention provides a device for determining the composition of a mixture of fluids that flow along a pipe, which comprises a radiation source for illuminating the mixture with radiation; a detector for detecting radiation that has been attenuated by the mixture; and a device for monitoring the flow rate of fluid along the pipe and outputting a signal indicative of the flow rate; the device including a device for adjusting the intensity of radiation emitted by the radiation source in response to the signal indicative of the flow rate so that the intensity of the radiation source is reduced if the flow rate reduces. It is noted that lifetime extension using power reduction is relatively small when a quartz halogen source is used, e.g. moving from maximum power to approximately 0.9 times maximum power will increase the life time by nominally ×5, after which the lifetime starts to decrease. The scope for lifetime extension is however considerably greater when this technique is used in combination with a broad band NIR source synthesised from solid state devices as is discussed below.

The invention also provides a method of determining the composition of a mixture of fluids that flow along a pipe, which comprises illuminating the mixture with radiation from a radiation source and detecting radiation that has been attenuated by the mixture; monitoring the flow rate of fluid along the pipe; and adjusting the intensity of radiation emitted by the radiation source in response to the flow rate determined so that the intensity of the radiation source is reduced if the flow rate reduces. In this way, output power of the radiation source may be controlled under feedback from the flow measurement so that it is never run at a power greater than the minimum required for satisfactory operation at a given flow rate.

BRIEF DESCRIPTION OF THE DRAWINGS

Various forms of device and method according to the invention will now be described by way of example, with reference to the accompanying drawings in which:

FIGS. 7a and 7b are schematic figures showing the operation of a digital mirror device employed in an embodiment of the invention;

DETAILED DESCRIPTION OF THE INVENTION

Figure 1:
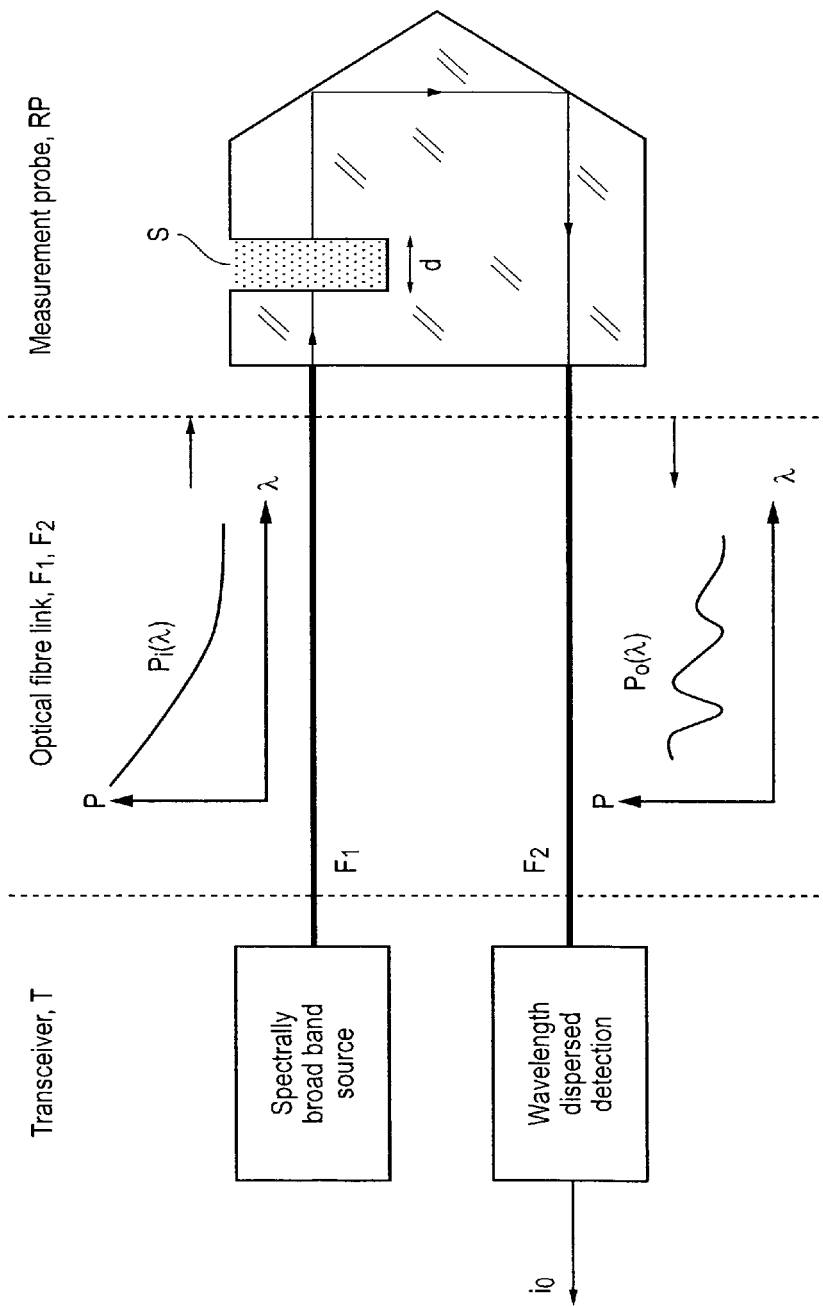
FIG. 1 is a schematic view of a measurement probe for determining the composition of a composition flowing in a pipe.

FIG. 1 is a schematic representation of a spectroscopic optical fluid analyser (SOFA) probe in which a spectrally broadband input source light distribution, $P_i(\lambda)$, is generated by transceiver T and sent along an optical fibre link $F_1$ to a Single Side Transmission (SST) retro-reflective measurement probe RP that is immersed in the specimen S. The SST probe may be replaced by a double sided transmission probe depending on the specific installation. In the measurement probe, the specimen is constrained to a depth d in the flow channel of the probe. After absorption of the radiation by the specimen, the radiation is reflected by the head of the probe and returned to the detector of the transceiver T by a second optical fibre $F_2$. The output power $P_o(\lambda)$ is spectrally attenuated as the result of broadband and molecular resonant absorption, and the output current of $i_o(\lambda)$ of the detected signal is given by, $$I_o = P_i(\lambda)\Gamma(\lambda)t_S(\lambda)[1-\sigma_m(\lambda)] \quad (7)$$

where, $\Gamma(\lambda)$ is the detector responsivity (Amp/Watt) as function of wavelength $\lambda$ $t_S(\lambda)$ is the Broadband spectral transmission of the specimen dependent on non-resonant effects (e.g. scatter); and $\sigma_m(\lambda)$ is the resonant molecular adsorption of the specimen.

A conventional spectrometer may be used for general detection and measurement of the absorption spectra as, for example, in a utility test system. However, a general spectrometer is preferably replaced, for reasons discussed above, by a component specific DOAS/rugate detection unit shown in FIGS. 3 and 4 described below.

The probe shown in FIG. 1 may employ a broadband radiation source derived, for example, from a conventional spectrally broadband incandescent source such as a quartz halogen lamp, or alternatively the broadband source may be synthesized by combining radiation from different sources. For example, radiation from a plurality of narrowband sources such as LEDs, super luminescent light emitting diodes (SLEDs), or thermorestive sources may be superimposed using a dichroic beam combiner, or any other suitable means for combining beams and coupled into the illumination optical fibre. Although such sources will couple less power into the fibre than a conventional lamp, and therefore may require the system to measure more slowly, they do have intrinsically longer lifetimes than which makes them suitable for applications such as sub-sea or subterranean measurement where the light source cannot be changed routinely. They may also be employed in other applications where the light source cannot easily be changed, for instance where the device is enclosed in a sealed unit that may be provided to prevent the risk of fire or explosion due to the presence of the hydrocarbon gases. They are also particularly suitable for life time extension using the modulation of the output power in response to variations in flow rate as discussed earlier. Yet another form of radiation source is a rugged incandescent ceramic radiation source, for example using a silicon nitride heating element. Such sources are compact, mechanically robust and low cost and emit radiation at wavelengths from 1 to 2 μm. They may typically be employed as gas igniters in domestic cookers and hobs.

Figure 2:
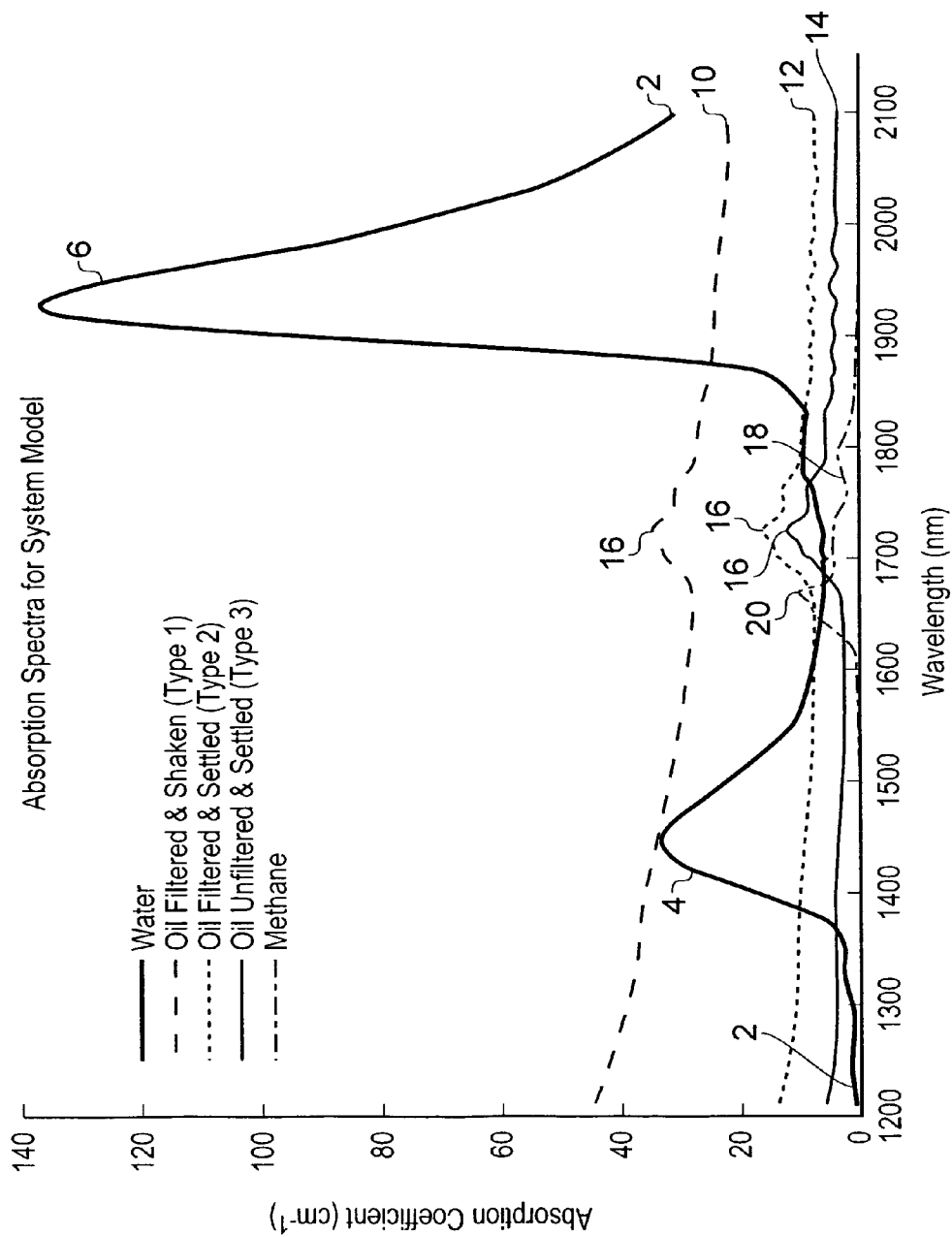
FIG. 2 shows a typical range of Near Infra Red (NIR) absorption spectra for oil, water methane.

FIG. 2 is an absorption spectrum that is typical for a mixture of hydrocarbons, optionally including gaseous hydrocarbons, and water that may be obtained in the bore of an oil well. The absorption spectrum may be made up of spectra from a number of components of the mixture. For example, spectrum 2 that is due to water exhibits an absorption peak 4 at approximately 1450 nm and extending from about 1400 to 1530 nm, and a second, larger, absorption peak at approximately 1930 nm. Three absorption spectra are shown for oil, curve 10 is the spectrum for filtered and shaken oil which may contain a number of small bubbles, for example containing air or gaseous hydrocarbons, that contribute to scattering of the radiation. Since the various different mixtures will be recorded by the spectrometer in rapid succession as the mixture flows along the pipe, the spectrum therefore will have a relatively large baseline caused by noise. Curve 12 is the spectrum for filtered and settled oil which has a significantly lower baseline due to the lack of air bubbles, while curve 14 is the spectrum of unfiltered and settled oil (type 3) with a relatively low baseline. Each of the spectra exhibits a hydrocarbon absorption peak 16 at approximately 1730 nm, extending from about 1700 to 1750 nm. In addition, it can be seen that the baseline of the curves is not flat, but is significantly larger at shorter wavelengths. Finally, curve 18 is the spectrum for methane or other low molecular weight gaseous hydrocarbons. This curve exhibits an absorption peak at approximately 1670 nm extending from about 1650 to 1690 nm.

Figure 3:
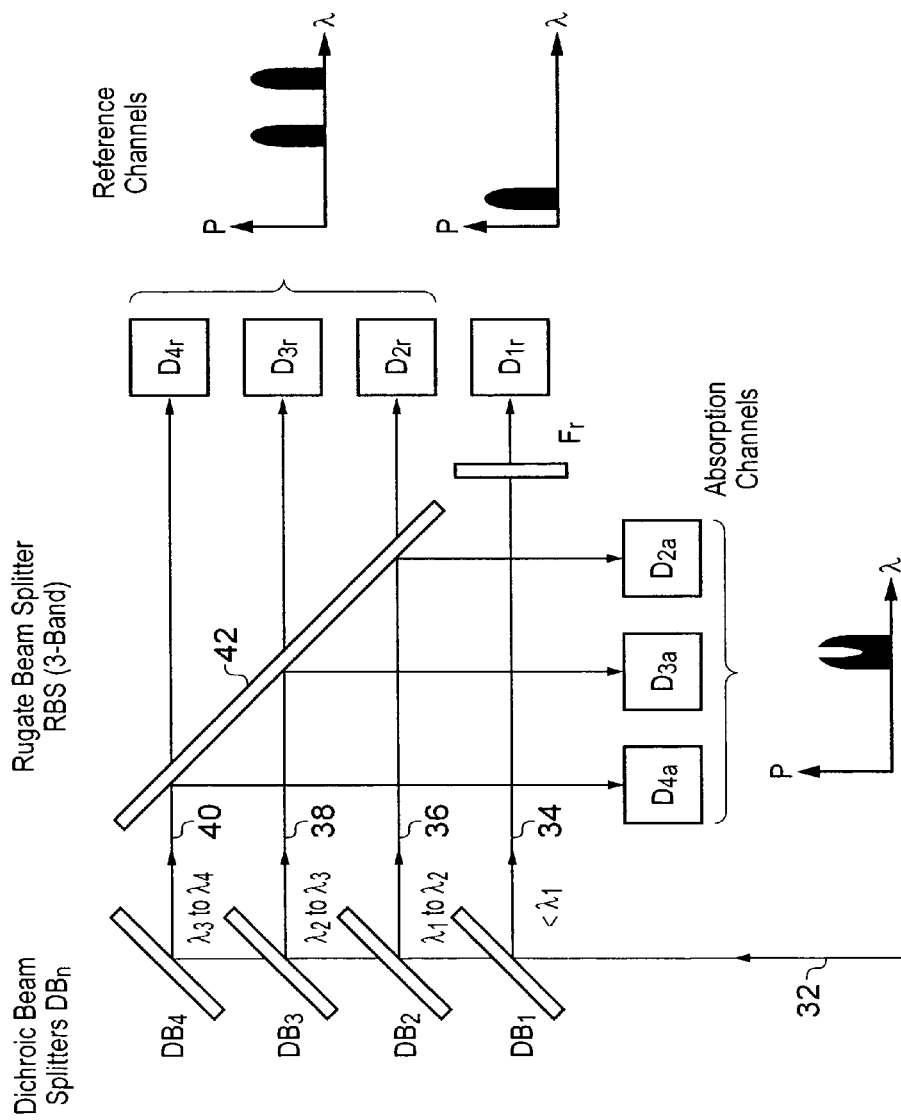
FIG. 3 is a schematic view showing a beam splitter employed in the device according to the invention.
Figure 4:
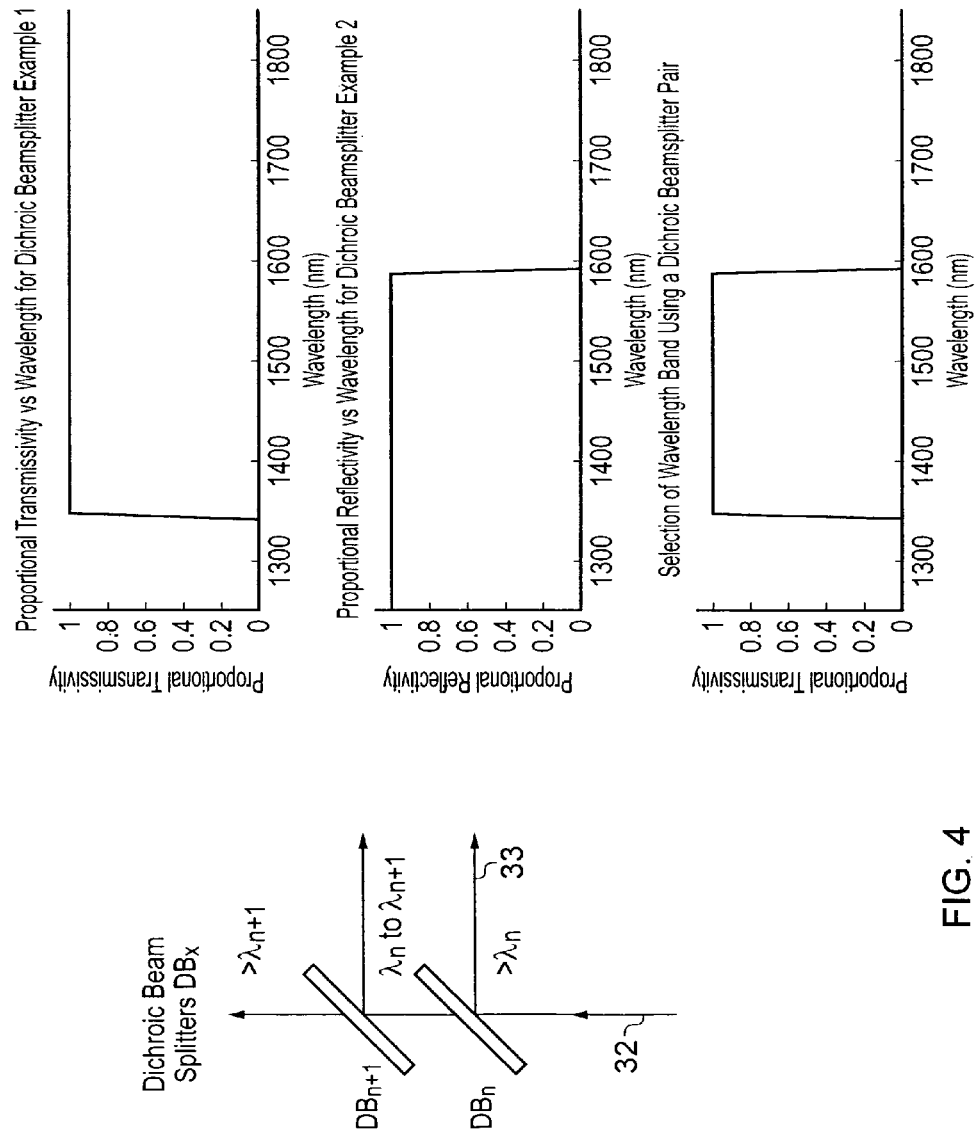
FIG. 4 shows the principle of operation of the dichroic beam splitters shown in FIG. 3.

FIG. 3 is a schematic view showing the principle of the present invention in which typical filter and Rugate wavelength bands (as indicated as a guideline below) enable referenced measurements of the NIR absorption bands of water, methane and oil defined above. This device comprises a series of dichroic beam splitters $DB_1$ to $DB_4$ that split a beam 32 of radiation from a spectrally broadband source (not shown) into a number of beams 34 to 40 of different wavelengths. In operation, the light from this source is first delivered to the measurement fluid by the optical fibre F1 and then delivered at 32 in FIG. 3 by the fibre F2 as shown in FIG. 1 after being spectrally modulated as a result of spectral absorption by the by the measurement fluid. The principle of beam splitting is shown in FIG. 4 where a broadband radiation source is passed to a first dichroic beam splitter $DB_n$ that transmits radiation of wavelength greater that a specified value $\lambda_n$, in this case 1345 nm, and reflects radiation of a wavelength below that value into beam 33. The transmitted beam is then sent to dichroic beam splitter $DB_{n+1}$ that transmits radiation of wavelength greater than a second wavelength $\lambda_{n+1}$, in this case greater than 1590 nm, and reflects radiation of wavelength less than $\lambda_{n+1}$ so that the radiation reflected by the second beam splitter will have a wavelength from 1345 to 1590 nm. In this way, the original beam is split into four beams having wavelengths less than 1345 nm, 1345 to 1590 nm, 1590 to 1690 nm and 1690 to 1825 nm respectively. The first beam 34 of wavelength less than 1345 nm is an overall reference channel which may be bandwidth limited by an additional notch filter $F_r$, and provides an auxiliary, non-resonant adsorption reference at nominally 1300 nm. as required.

Figure 5A:
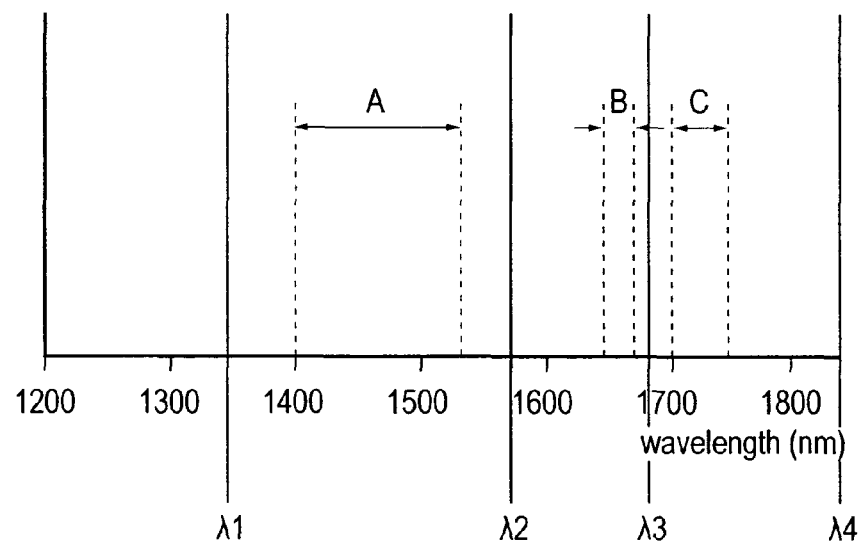
FIG. 5 shows filter characteristics of a Rugate beam splitter employed in the device according to the invention.
Figure 5B:
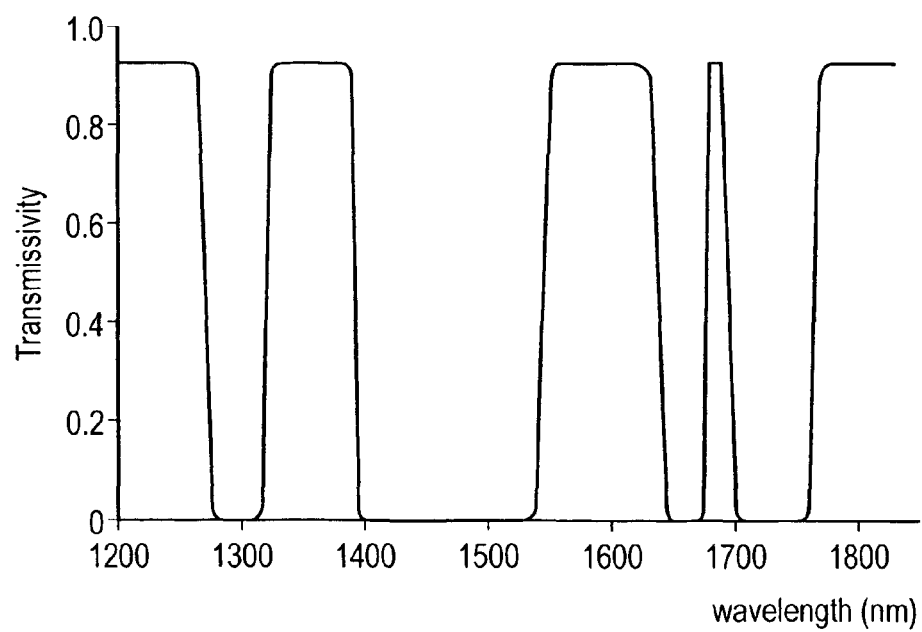

The remaining beams 36, 38 and 40 each have wavelengths corresponding to an absorption band of interest and also wavelengths that are outside, but adjacent to, the absorption bands. These beams are passed to a Rugate beam splitter 42 having a characteristic shown schematically in FIGS. 5 (a) and (b). In principle, any optical notch filter having the appropriate characteristic may be employed, for example a dielectric quarter-wave stack, but Rugate notch filters have the advantage that they exhibit significantly lower amplitude higher-order harmonic structure in the Rugate notch. The Rugate notch filter 42 will reflect that part of beam 36 having wavelengths of 1400 to 1530 nm, shown as region A in FIG. 5a, corresponding to the water absorption band, into detector $D_{2a}$ and transmit the remaining parts of the beam, i.e. of wavelength 1345 to 1400 nm and 1530 to 1590 nm into detector $D_{2r}$ to provide a reference. Similarly, the Rugate notch filter will reflect that part of beam 38 having wavelengths of 1650 to 1690 nm, shown as region B in FIG. 5a corresponding to the gaseous hydrocarbon (methane) absorption band, into detector $D_{3a}$ while transmitting the remaining parts of the beam into the reference detector $D_{3r}$. Finally, the Rugate notch filter will reflect that part of beam 40 having wavelengths of 1700 to 1750 nm, shown as region C in FIG. 5a, corresponding to the oil absorption band, into detector $D_{4a}$, while transmitting the remaining parts of the beam, i.e. of wavelengths 1690 to 1700 nm and 1750 to 1800 nm into reference detector $D_{4r}$. In this way, the device according to the invention allows the intensity of the radiation attenuated by the water, methane and oil absorption bands respectively to be detected, and to detect the intensity of non-resonant reference signals on each side of the absorption bands.

The above wavelengths give a general indication of those that would be used specifically for DOAS water, methane and oil measurement. They may in practice be modified for optimum operation and in particular may be modified to enable the measurement of water using the absorption band centred at nominally 1950 nm. The wavelengths will be changed entirely when the same general principle is used for the measurement of different molecular constituents.

The values for attenuation of the radiation detected by the reference detectors on either side of the absorption bands may simply be averaged in order to provide a baseline for the absorption bands. In view of the wavelength dependency of the background absorption of the radiation shown in FIG. 2, the baseline for the absorption bands may not be the same for each band. Further, where the absorption band extends over a significant wavelength range, the baseline for the absorption may not be horizontal but may be formed as a straight-line interpolation of the intensity measured by the reference detector on either side of the absorption band.

It is not necessary to employ a number of dichroic beam splitters to divide an original beam into a number of separate beams of smaller wavelength range, and to pass each divided beam through a Rugate filter as described above. Other arrangements may be employed instead. For example, one or more Rugate filters may be used to divide the original beam into beams of different wavelengths and the separate beams may be passed to one or more dichroic beam splitters or to a further Rugate filter that is different from the first Rugate filter in order to form separate absorption and reference beams. Similarly, it is possible to split the original beam into the appropriate wavelength ranges using only dichroic beam splitters. On the other hand, it is possible to use dielectric quarter-wave stacks instead of rugate notch filters as mentioned above.

Figure 6:
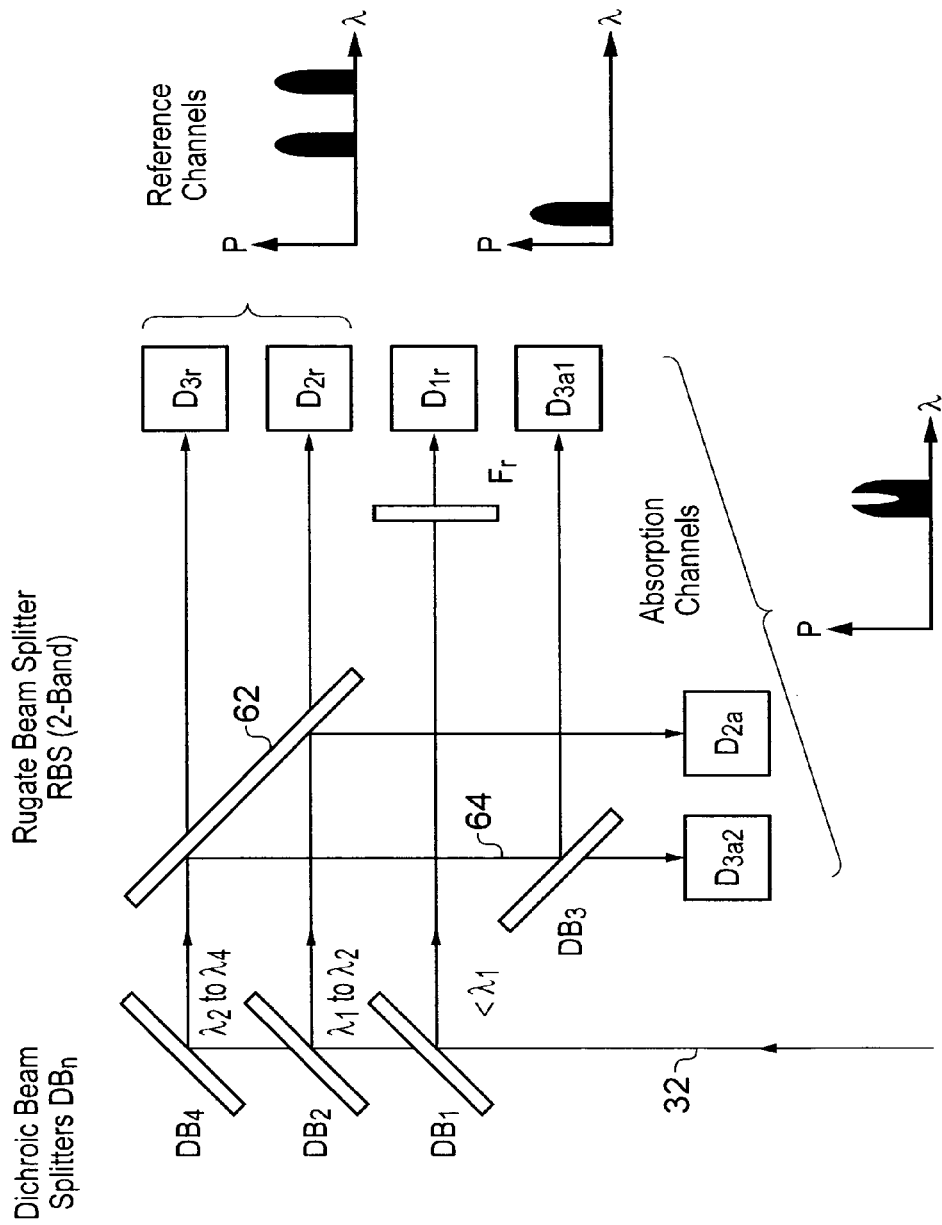
FIG. 6 is a schematic view showing the principle of an alternative form of beam splitter according to the invention.

It is not essential to the invention that the reference detectors detect the radiation intensity on both sides of each absorption peak. It is possible, for example for the reference detectors to detect the radiation on each side of a pair of absorption bands or on each side of all three absorption bands and to average or interpolate the baseline if necessary using the reference signals. FIG. 6 shows an alternative arrangement in which reference absorption is detected on each side of a pair of absorption bands. The purpose of this arrangement is to simplify the design of the Rugate by reducing the number of spectral notches. In this arrangement, the original broadband radiation beam 32 is split by three dichroic beam splitters $DB_1$ to $DB_3$ into beams 60, 62 and 64, the first of which has a wavelength less than $\lambda_1$ (1345 nm) and is filtered by a notch filter $F_r$ as described above to provide an auxiliary, non-resonant absorption reference at nominally 1300 nm as required. The transmitted beam is split by beam splitter $DB_2$ to reflect radiation of wavelength less than $\lambda_2$ (1590 nm) and is passed to the rugate beam splitter 62 in the manner described above to split the radiation so that radiation having a wavelength of 1400 to 1530 nm corresponding to the water absorption band can be detected by detector $D_{2a}$ and reference bands having wavelengths of 1345 to 1400 nm and 1530 to 1590 nm are detected by detector $D_{2r}$ as described above. The radiation that is transmitted by dichroic beam splitter $DB_2$ having a wavelength greater than $\lambda_2$ (1590 nm) is passed to dichroic beam splitter $DB_4$ which reflects radiation of wavelength below $\lambda_4$ (1825 nm) corresponding to both the oil and gaseous hydrocarbon component absorption bands onto the rugate beam splitter 62. Radiation of wavelength below 1650 nm and above 1750 nm is transmitted by the Rugate beam splitter 62, into detector $D_{3r}$ to detect the reference background radiation intensity on each side of the pair of absorption bands for oil and gaseous hydrocarbons. Beam 64 that is reflected by the rugate beam splitter 62 and has wavelengths of from 1650 to 1750 nm is passed to dichroic beam splitter $DB_3$ that reflects radiation of wavelength below $\lambda_3$ (1690 nm), corresponding to the methane absorption band, into detector $D_{3a1}$ and transmits radiation of wavelength above $\lambda_3$ corresponding to the oil absorption band, into detector $D_{3a2}$.

This simplification of the Rugate component is expected to reduce the cost of the overall system.

It is noted that an identical source and detection system may be used in combination with other designs of probe such as double pass transmission and ATR (Attenuated Total-internal Reflection).

One limitation with employing broadband light sources such as incandescent sources is that it is difficult to modulate them electronically at the frequencies required for effective compensation of the dark current noise of the near infrared detector (for example an InGaAs detector). To overcome this limitation an external device may be used to modulate the light field. For example, the invention as described may, for this purpose, use a compact spatial light modulator (SLM) in which a digital mirror device (DMD) provides an intrinsically high speed and high contrast on/off ratio. This is shown in principle in FIG. 7a and FIG. 7b.

In FIG. 7a, lens $L_1$ forms an image of the output aperture of the source S in the plane of the aperture $L_2$ via reflection of the beam by the DMD, and $L_2$ images the output aperture of $L_1$ in the plane of the output optical fibre F that couples light to the sensor probe immersed in the fluid. The apertures and focal lengths of $L_1$ and $L_2$ are chosen to match optimally the phase volume of the source to that of the fibre.

The DMD consists of an array of multiple square mirrors (in this case approximately 7 μm×7 μm) each of which can be individually actuated as shown in FIG. 7b to switch between angular orientations +θ (position a) and −θ (position b) via the neutral position b (θ=0). In operation the light field coupled into the output fibre is modulated by simultaneously switching all of the mirrors in the array between the +θ and −θ position corresponding to the on state in which the radiation is coupled into the output fibre F and the off state in which the light is reflected into a beam dump D. The modulation rate may be as high as 6.5 kHz or more by virtue of the DMD. The DMD may be employed with any form of incandescent light source, but it is particularly convenient to use it with the ceramic radiation source referred to above.

The design of device shown in FIGS. 3 and 6 in which the radiation is reflected by the rugate filters at a 45° degree angle of incidence can have the disadvantage that the s and p polarisation components of randomly polarised light delivered from the sensing probe may have different filter transmission responses that result in spectral blurring and ringing of the light transmitted or reflected by a given filter. This could be eliminated by the use of a polarising filter, but this would entail a minimum 50% light loss and efficacy over a limited wavelength range. These effects can, however, be eliminated or substantially eliminated over the full operating wavelength range without significant light loss by limiting the angle of incidence to a maximum value of not more than 20° and preferably not more than 15° (to the normal to the plane of the filter).

In one preferred design of device an image of the light field 32 at the aperture of the input fibre connected to the probe output is formed at the detector apertures S1 to S5 by selected lenses in the lens chain L1 to L8 and hence via transmission and reflection at selected filters and Rugates within this chain. In this arrangement the light first passes through NRF1 and then NRF2 via the broadband, high efficiency front reflecting mirrors IM to be incident on the long pass filter LP1. The purpose of the filters NRF1 and NRF2 is to reject low and high out of band spectral noise at the sensor input. The long wavelength component of the light transmitted by LP1 passes to the Rugate filter R1 where it is divided into the transmitted and reflected components. The former forms the reference bands for the oil/methane measurement after transmission through the trimming short pass filter TSP1 which suppresses the longer wavelengths present. The latter is reflected by the double sided mirror DM via lens L4. Light reflected by the mirror DM is again reflected by the Rugate R1 and mirror DM before being passed to low pass filter LP2 which transmits light of wavelength of the oil absorption band to the trimming band pass filter TPB3 which spectrally limits light of the oil absorption band, and finally to sensor S3 for detecting the oil concentration. Light reflected by the low pass filter LP2 has a wavelength corresponding to the methane absorption band and is passed to the trimming band pass filter TBP2 and hence to sensor S2 for determining the amplitude of the methane peak.

Light reflected by the long pass filter LP1 is incident on Rugate R2 which transmits light of the water reference wavelength to the water reference frequency detector S4 via trimming short pass filter TSP4 which suppresses long wavelength of the water reference band. Light of wavelength of the water absorption band is reflected by the Rugate R2 back to the double sided front reflection mirror DM whereupon it is reflected back to the trimming band pass filter TBP5 for the water measurement and detector S5 for detecting the water absorption peak.

In this detector, the sensor may be configured to measure either methane and oil combined at detector S2/3 by an optical flat, broadband anti-reflection element coated on both faces which has a high transmission for both methane and oil absorption bands, or to measure oil at detector S2 and methane at detector S2 by the use of the low pass filter LP2.

In this design of detector, the Rugate R1 and the double sided front mirror DM may be separated by a significant distance, for example in the range of 30 to 50 mm so that the light beams will be spaced apart laterally by a sufficient distance to enable detectors S1 and S2 or S3 to be used, and to enable different detectors S4 and S5 to be used while keeping the angle of incidence of the light rays at the various filters and mirrors at a low value of about 15°.

Figure 8:
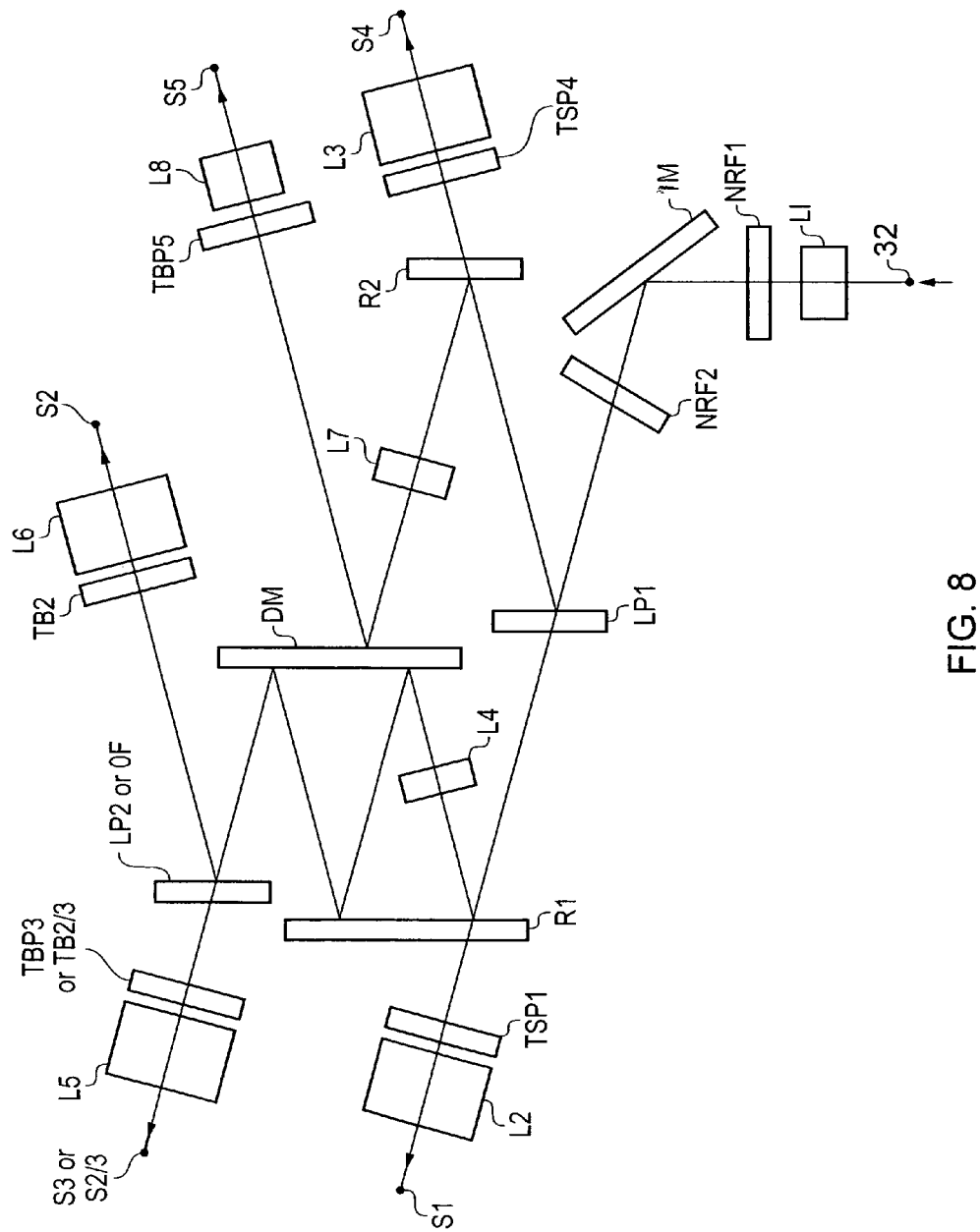
FIG. 8 is a schematic view of an alternative embodiment in which the angle of the light beam at the filters is reduced.
Figure 9:
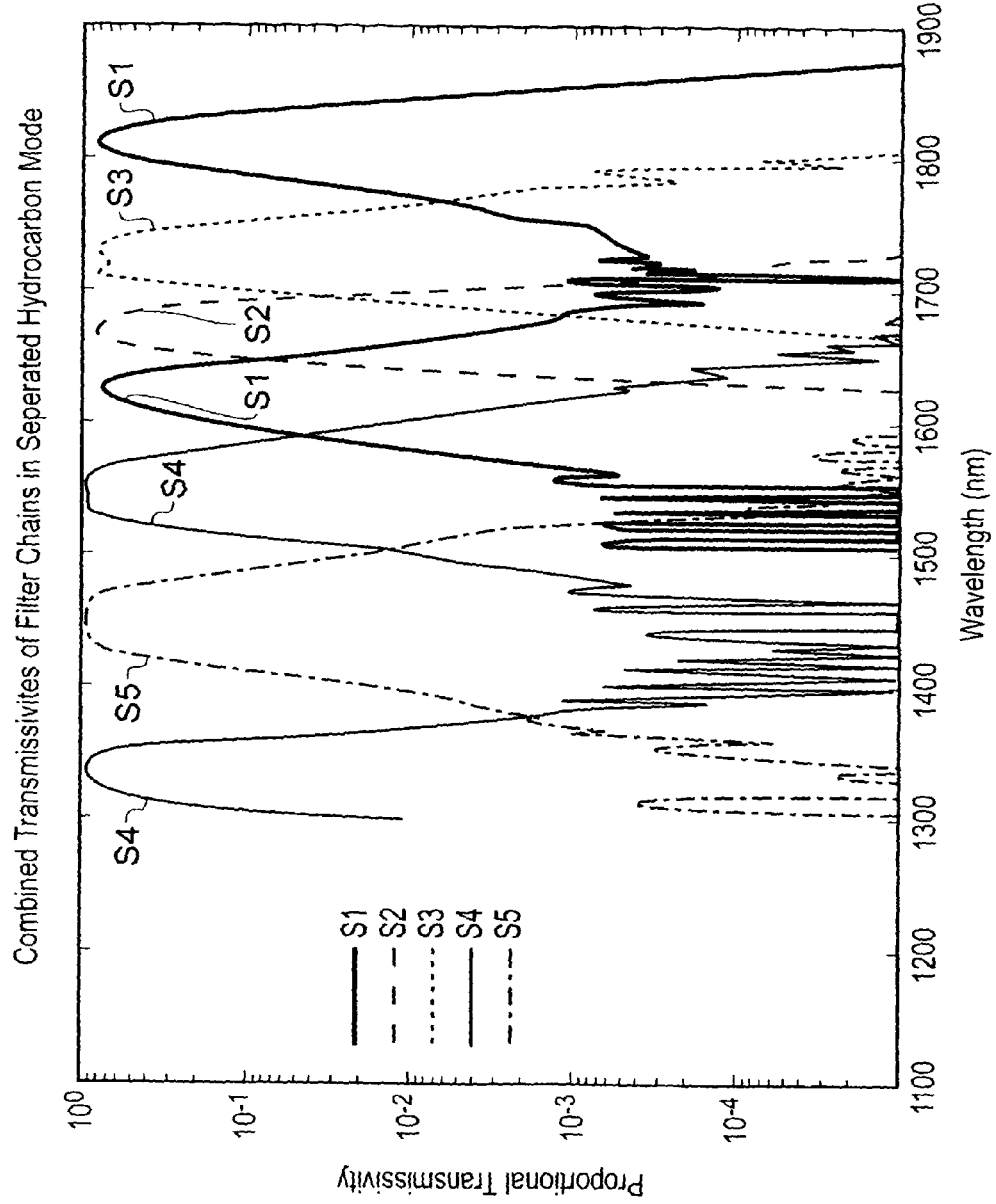
FIG. 9 is a graphical representation of the transmissivities of the system at the detectors of the embodiment of FIG. 8.

FIG. 9 shows the concatenated spectral transmissivity of each of the channels S1 to S5 of the arrangement shown in FIG. 8 obtained by multiplying the spectral reflectances/transmissivities of each component within a given channel. As can be seen, the transmissivity peak for the detector S5 (1400 to 1510 nm) corresponding to water absorption is bounded on each side by transmissivity peaks at 1300 to 1380 nm and at 1510 to 1590 nm for the detector S4 which peaks are used as references for the water detection peak observed by detector S5. Similarly, detector S2 has a transmissivity peak at 1650 to 1690 nm, which detects the presence of methane, and detector S3 has a transmissivity peak at 1700 to 1750 nm which detects the presence of oil. This pair of transmissivities is bounded by a pair of transmissivity peaks occurring at 1590 to 1650 nm and at about 1770 to 1850 nm which are used as references for determining the value of the methane and oil absorption peaks. As can be seen, the arrangement according to the invention enables the reference bands employed to determine the intensity of the water and the hydrocarbon absorption bands to abut the bands, and the peak value for the transmissivity values for the references will normally be not more than 150 nm and especially not more than 100 nm from the peak value for the absorption bands. A general aim is to make the reference beams symmetrical about the absorption bands in order to minimise errors due to the spectral gradient of the background signal.

Figure 10A:
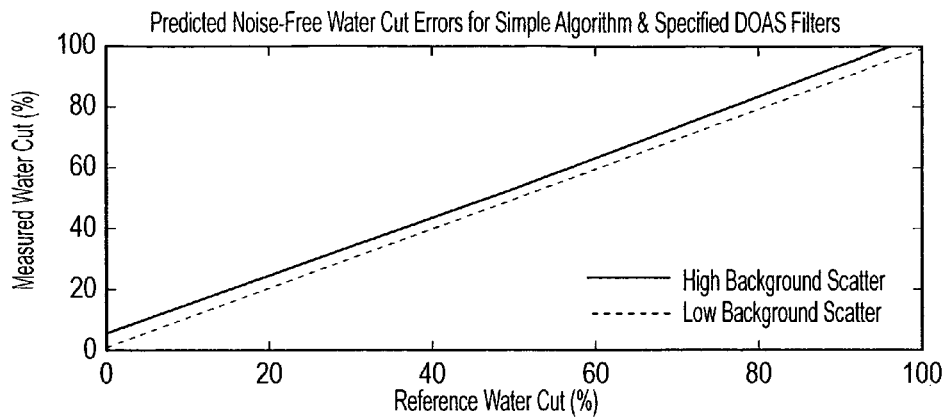
FIG. 10 is a graphical representation of the errors in the water cut determination of the embodiment according to the invention and a device employing remote referencing.
Figure 10B:
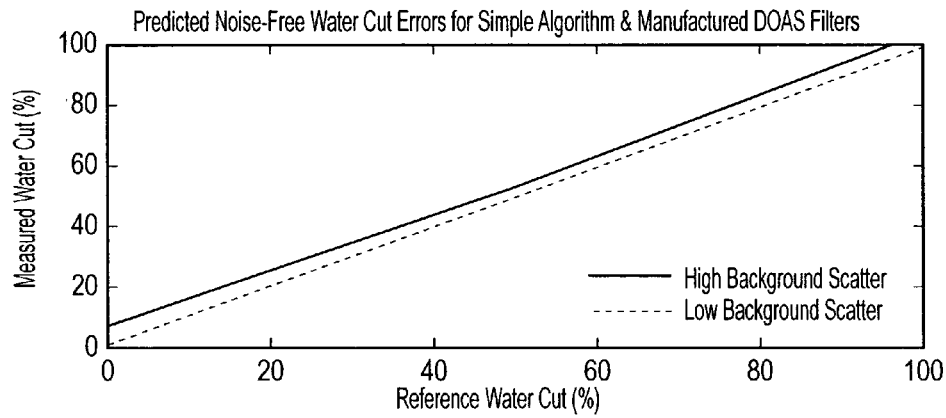
Figure 10C:
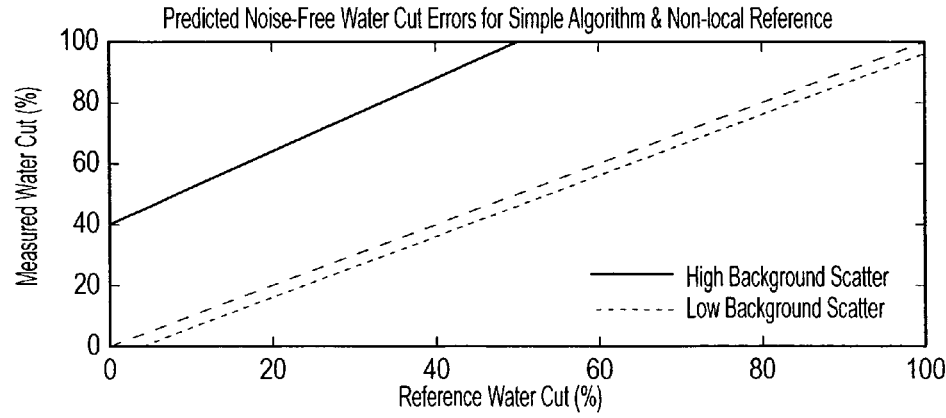
Figure 11:
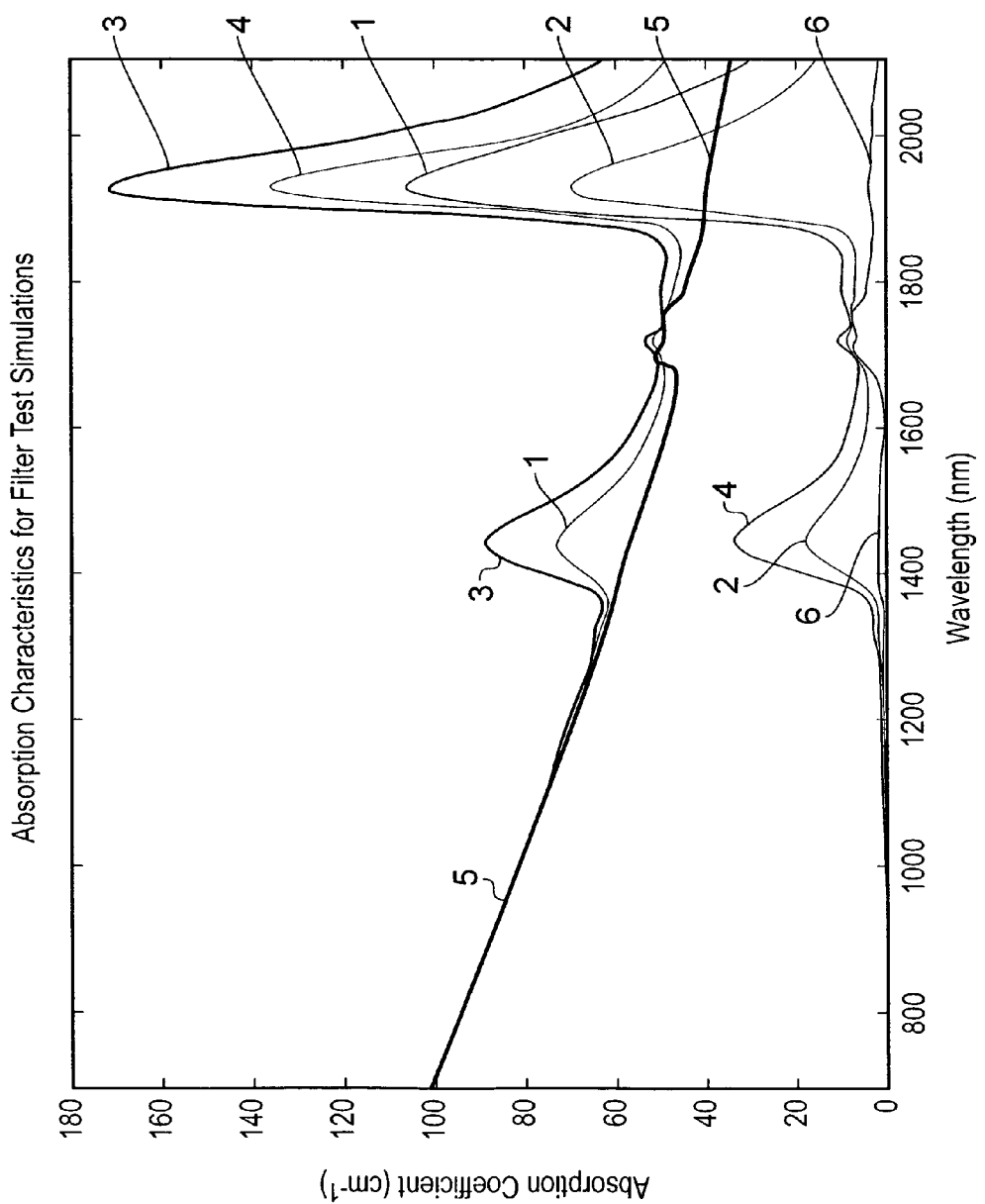
FIG. 11 is a graphical representation of the absorption of the mixtures used in generating the errors shown in FIG. 10.

The improvement in accuracy obtained by local referencing, i.e. by determining the absorption due to the presence of water and hydrocarbons with reference to the absorption at a wavelength that is adjacent to the absorption peaks is shown in FIGS. 10 and 11. FIG. 11 is an absorption spectrograph for six mixtures of hydrocarbon and water at three different values for the water cut ($W_c$) and at two different values for the background scatter due to turbulence, as follows:

Mix 1: $W_c$=50%; High background
Mix 2: $W_c$=50%; Low background
Mix 3: $W_c$=99%; High background
Mix 4: $W_c$=99%; Low background
Mix 5: $W_c$=1%; High background
Mix 6: $W_c$=1%; Low background.

These fluids were used for determining the filter/reference performance simulations shown in FIG. 10. The graph shown in FIG. 11 is similar to that shown in FIG. 2 but somewhat more accurate. The curve for mix 6 has the lowest value because the hydrocarbons have lower absorption than that of water, and there is relatively little scatter due to turbulence. The curve for mix 5 shows a strong wavelength dependency due to Rayleigh and Mie scatter. The remaining curves show water absorption peaks depending on the water cut (Wc) superposed on a baseline that decreases with wavelength due to scatter.

The results for the measured water cut values given against reference water cut values at low and high values of background scatter are shown graphically in FIG. 10. FIGS. 10a and 10b show predicted noise-free values of the water cut against reference values for both low and high background scatter (caused by small particles or bubbles in the mixture) employing an algorithm based on equation 1 incorporating calibration terms for 100% water and 100% oil in the probe.

FIG. 10c is a similar graph showing the values for low and high background scatter obtained using a system that employs a remote reference as in U.S. Pat. No. 6,292,756. The dotted straight line in each of the graphs extending linearly from 0% to 100% measured and reference water cut shows the actual value of the water cut. The upper two graphs, demonstrating a system according to the present invention with local referencing, have an error in the water cut value due to the presence of scatter background which is less than 4% even when obtained with high background scatter, whereas the equivalent error in the water cut value using a system with remote referencing is in excess of 40%. For results obtained using non-local referencing, even in the case of low background scatter the output departs from the "truth" line (where the measured water cut is equal to the reference water cut). The close correlation between the outputs shown in FIGS. 10a and 10b obtained respectively for the theoretical and manufactured spectral transmissivity of the filters (c.f. FIG. 9) demonstrates the practical feasibility of the overall system.

Figure 12:
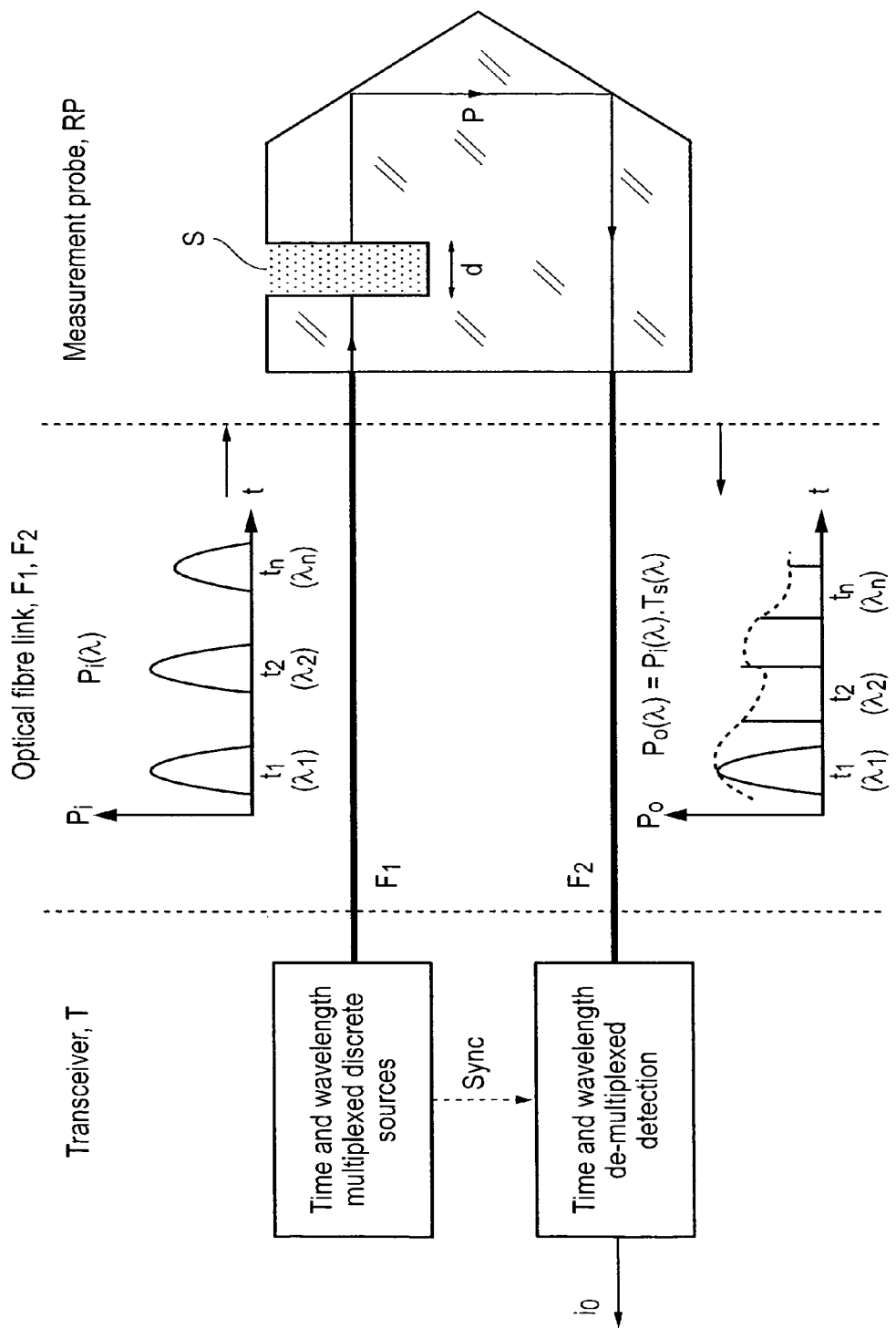
FIG. 12 is a schematic view of an alternative form of measurement probe in which a number of narrowband radiation sources are time multiplexed.

While it is preferred for the measurement probe to employ a broadband radiation source, either formed from a single device or from a number of narrowband devices, as shown in FIG. 1, it is possible to employ a number of time-multiplexed narrowband or quasi narrowband sources as shown in FIG. 12. Radiation from a number of discrete sources centred at wavelengths $\lambda_1$ to $\lambda_n$ with corresponding bandwidth $\Delta\lambda_n$ is time and wavelength multiplexed to propagate sequentially at times $t_1$ to $t_n$ through the system. The power transmitted by the specimen at each wavelength is measured sequentially at times $t_1$ to $t_n$ using time and wavelength de-multiplexed detection. The detection electronics are synchronised with the time multiplexed input signal. This enables the source and hence wavelength at which the absorption is measured to be identified. The spectral distribution of the input sources (i.e. either a Light Emitting Diode: LED, Laser Diode: LD, or Super Luminescent Light Emitting Diode: SLED), may be selected to match the spectral ranges employed in the measurement. Under these conditions a Rugate beam splitter system may be used in combination with time de-multiplexing of the signals detected by the photodetectors for absorption in the relevant bands of the liquid, the reference bands and subsidiary reference detection (~1300 nm). The ratio of the absorption to reference signals recorded in corresponding time slots generate the DOAS signal required for the measurement of the concentration of water, methane and oil in the presence of spectrally broad band variations in absorption.

Figure 13:
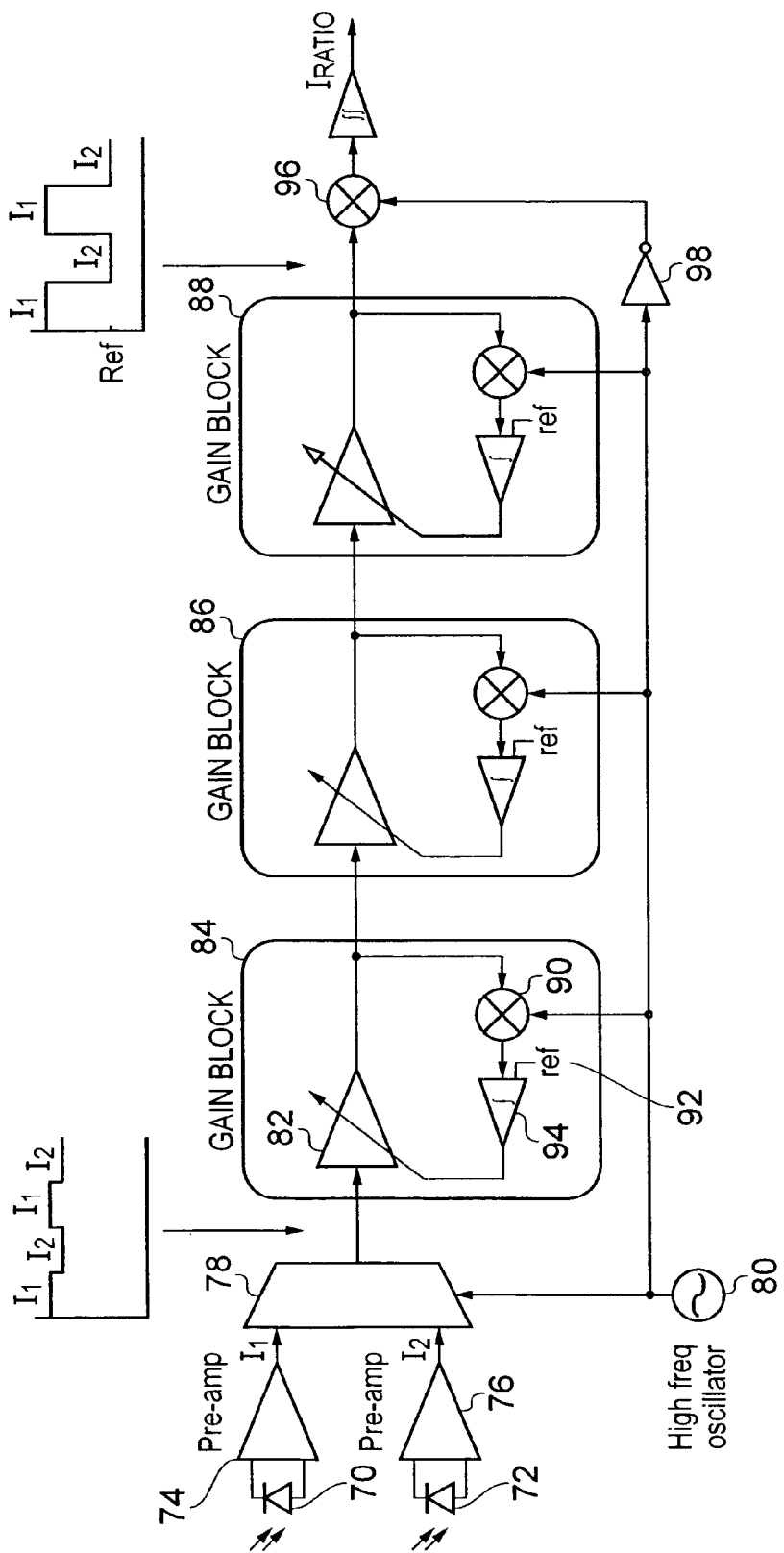
FIG. 13 is a schematic of the signal processing circuit for determining the absorption of radiation by a fluid using a device shown in FIGS. 1 to 9.

FIG. 13 is a schematic showing an electronic circuit that may be employed to process the radiation intensity signals that are generated by the detectors $D_{na}$ and $D_{nr}$ of the device. One problem with the output of the detectors of the device is that the background signal on which the absorption band signals are superposed can have a very large dynamic range that may be significantly greater than the differences between the absorption bands, and which varies rapidly with time. This has the result that, if a conventional circuit were used, an extremely high resolution analogue-to-digital converter would be required to cover the full dynamic range of the signals while being sensitive enough to measure small differences between the signals. The circuit that is employed according to this aspect of the invention has the advantage that lower cost components may be used while having the required bandwidth do deal with changes in the signal intensities.

The circuit comprises a pair of a pair of photodetectors 71 and 72 forming absorption detectors $D_{na}$ and reference detectors $D_{nr}$ respectively for detecting the absorption band attenuated radiation intensity and the reference radiation intensity for one absorption band. Additional circuits corresponding to the circuit shown in FIG. 4 are required to detect the intensity of the other absorption bands. The detectors may be for example a pin photodiode or an avalanche photodiode as is conventional. The outputs from the photodetectors 70 and 72 are fed into preamplifiers 74 and 76 whose output is fed into time division mulitiplexer 78. The outputs $I_1$ and $I_2$ of the preamplifiers 74 and 76 respectively are chopped alternately with the output of a high frequency oscillator 80 to give a square wave alternately proportional to $I_2$ and $I_1$, and the output is fed into the input of a variable gain differential amplifier of a closed-loop gain block 84. Time-division multiplexing of the outputs $I_1$ and $I_2$ is performed so that the same gain can be applied both outputs by the differential amplifier 82. The output from gain block 84 is fed into a second gain block 86. As shown, three gain blocks are employed, but more or fewer may be used as is necessary in order that the circuit is capable of handling the dynamic range of the variations in intensity of the detected radiation. The purpose of the gain blocks is to reduce the dynamic range of the signals to a manageable level while preserving the ratio information of $I_1$ and $I_2$.

In the initial gain stage 84, where the input is the chopped square wave of $I_1$ and $I_2$, an amplified version of the input formed by the amplifier 82 is demodulated with the oscillator signal by demodulator 90 to give just $I_2$. The signal $I_2$ from the demultiplexer is filtered with respect to a reference signal 92 by means of an integrating amplifier 94. The output of the integrating amplifier, which will be proportional to $I_2$, is used to set the gain of the amplifier 82, for example by means of a servo, so that:

$$G \cdot I_2 = \text{ref}$$

where G is the gain of amplifier 82 and ref is the reference voltage.

The gain G is thus inversely proportional to the value of $I_2$, or $$G = \frac{ref}{I_2} \qquad (8)$$

In the case of an amplifier circuit formed from a number of gain stages 84, 86 and 88, in which the gain of each of the gain stages is set with reference to the reference voltage ref, the total gain, $G_T$ is given by equation 2.

The signal is then demodulated by demodulator 96 using the anti-phase of the oscillator 80 formed by inverter 98 to remove $I_2$ and leave $I_1$ as the input to the amplifier. The signal output by the overall amplifier is thus $G_T \cdot I_1$ which is given by $$G_T I_1 = \frac{I_1 \cdot ref}{I_2} \qquad (9)$$

Since ref is known, and the same gain has been applied to both $I_1$ and $I_2$, the required ratio $I_1/I_2$ can be calculated in the digits from the output signal $G_T I_1$. The output of the circuit is thus not dependent on the rapidly time-varying background signal, but only on the relatively slowly varying ratio $I_1/I_2$ which has a much smaller dynamic range than the absolute value of the individual absorption bands.

The invention claimed is:

1. A device for determining the composition of a predefined mixture of fluids by spectral absorption, which comprises:
    a radiation source for illuminating the mixture with radiation having a range of wavelengths that extends over a predefined absorption band of each one of said fluids and over at least one predefined reference band outside, but adjacent to, each one of said absorption bands;
    a separating device configured for separating the radiation that has been attenuated by the mixture;
    a detector for detecting the radiation after separation by said separating device; wherein said separating device comprises:
    a first radiation divider configured for separating said radiation into different wavelength bands, each one of which extending over the absorption band of a corresponding one of said fluids and over at least one of said reference bands adjacent to said absorption band; and
    a second radiation divider configured for receiving from said first radiation divider the radiation corresponding to each one of said different wavelength bands and for further separating it into a wavelength band corresponding to the respective said absorption band and a wavelength band corresponding to the respective at least one of said reference bands.

2. A device as claimed in claim 1, wherein the separating device comprises a dichroic beam splitter and/or a rugate notch filter.

3. A device as claimed in claim 2, wherein said first radiation divider includes a plurality of dichroic beam splitters to split the radiation into a plurality of wavelength bands, and said second radiation divider includes a rugate notch filter configured for splitting the radiation in each wavelength band into an absorption band and a reference band having a wavelength range adjacent to the absorption band.

4. A device as claimed in claim 3, which is arranged so that radiation impinges on the dichroic beam splitters and/or rugate notch filters at an angle of incidence of not more than 20°.

5. A device as claimed in claim 1, wherein the radiation source is a broadband radiation source that is operable to emit radiation over the entire range of absorption bands of the fluids.

6. A device as claimed in claim 1, which includes a digital mirror device for modulating radiation from the radiation source.

7. A device as claimed in claim 1, which is operable to multiplex radiation from a plurality of narrowband radiation sources to generate the radiation, and the detector is operable to demultiplex the detected radiation.

8. A device as claimed in claim 1, wherein said first radiation divider separates said radiation through splitting said radiation into distinct beams, each beam including a respective one of said wavelength bands.

9. A device as claimed in claim 8, wherein said second radiation divider receives each beam of said distinct beams and split said beam into two further distinct beams, a first beam of said two further beams including a wavelength band corresponding to the respective said absorption band, a second beam of said two further beams including a wavelength band corresponding to the respective at least one of said reference bands.

10. A method of determining the composition of a mixture of fluids by spectral absorption, which comprises the steps of:
- illuminating the mixture with radiation from a radiation source having a range of wavelengths that extends over an absorption band of each one of said fluids and over at least one reference band outside, but adjacent to, each one of said absorption bands;
- separating the radiation that has been attenuated by the mixture into different wavelength bands, each one of which extending over the absorption band of a corresponding one of said fluids and over at least one of said reference bands adjacent to said absorption band;
- further separating the radiation corresponding to each one of said different wavelength bands into a wavelength band corresponding to the respective said absorption band and a wavelength band corresponding to the respective at least one of said reference bands;
- detecting the radiation after said separation steps.

11. A method as claimed in claim 10, wherein said step of separating the radiation that has been attenuated by the mixture comprises separating the radiation into two of said reference bands located adjacent and on opposite sides of the absorption band of one of the fluids.

12. A method as claimed in claim 11, wherein said two reference bands are located substantially symmetrically on either side of said absorption band.

13. A method as claimed in claim 11, wherein it includes the step of interpolating the level of absorption of the radiation in said two reference bands in order to generate a baseline for the corresponding absorption band.

14. A method as claimed in claim 10, wherein the radiation is separated into at least three absorption bands.

15. A method as claimed in claim 10, wherein said separations are made by means of a dichroic beam splitter and/or a rugate notch filter.

16. A method as claimed in claim 15, wherein the separation into different wavelength bands is made by means of a plurality of dichroic beam splitters, and the separation of each wavelength band into absorption band and reference band is made by means of a rugate notch filter.

17. A method as claimed in claim 10, wherein the mixture comprises water and hydrocarbons.

18. A method as claimed in claim 10, wherein said step of separating the radiation comprises a step of splitting said radiation into distinct beams, each beam including a respective one of said wavelength bands.

19. A method as claimed in claim 18, wherein said step of further separating the radiation comprises a step of receiving each beam of said distinct beams and split said beam into two further distinct beams, a first beam of said two further beams including a wavelength band corresponding to the respective said absorption band, a second beam of said two further beams including a wavelength band corresponding to the respective at least one of said reference bands.

* * * * *